United States Patent [19]

Hsu et al.

[11] Patent Number: 4,524,142

[45] Date of Patent: Jun. 18, 1985

[54] PLATINUM (O) COMPLEX-BASED HYDROFORMYLATION CATALYST

[75] Inventors: Chao-Yang Hsu, Media; James E. Lyons, Wallingford; Paul E. Ellis, Jr., Downingtown, all of Pa.

[73] Assignee: Sun Tech, Inc., Philadelphia, Pa.

[21] Appl. No.: 598,931

[22] Filed: Apr. 11, 1984

[51] Int. Cl.$^3$ .................. B01J 31/12; B01J 31/22; B01J 31/24

[52] U.S. Cl. ................... 502/153; 502/154; 502/155; 502/162; 568/454; 568/909

[58] Field of Search ............ 502/153, 154, 155, 162

[56] References Cited

U.S. PATENT DOCUMENTS

| | | | |
|---|---|---|---|
| 3,876,672 | 4/1975 | Mrowca | 260/604 HF |
| 3,981,925 | 9/1976 | Schwager et al. | 502/162 |
| 3,996,293 | 12/1976 | Knifton | 502/169 X |
| 4,101,565 | 7/1978 | Poist | 502/162 |
| 4,155,939 | 5/1979 | Poist | 260/604 HF |
| 4,256,616 | 3/1981 | Hatanaka et al. | 502/162 X |
| 4,370,258 | 1/1983 | Ogata et al. | 502/162 |
| 4,405,496 | 9/1983 | Hsu | 502/169 X |

FOREIGN PATENT DOCUMENTS

| | | | |
|---|---|---|---|
| 56-118034 | 9/1981 | Japan | 502/162 |
| 57-134495 | 8/1982 | Japan | 502/162 |

OTHER PUBLICATIONS

Kirk-Othmer, *Encyclopedia of Chemical Technology*, (Third Edition) vol. 16, pub. by John Wiley & Sons, N.Y., N.Y., pp. 637-653.
JACS, 97, 3553 (1975).
J. of Cat., 45, pp. 256-267 (1976).
JCS-Chem. Comm., pp. 462-463 (1979).

*Primary Examiner*—Patrick P. Garvin
*Attorney, Agent, or Firm*—J. Edward Hess; Donald R. Johnson; Stanford M. Back

[57] ABSTRACT

Olefins are hydroformylated with syngas in the presence of a novel organometallic complex catalyst to form the corresponding aldehydes at high reaction rates and improved selectively of linear aldehydes over branched aldehydes.

The novel catalyst comprises an organometallic complex formed from a mixture of
  (1) a platinum (O) complex containing two bidentate diphosphine, diarsine or distibine ligands; and
  (2) A Group IVB metal halide.

12 Claims, No Drawings

PLATINUM (O) COMPLEX-BASED HYDROFORMYLATION CATALYST

BACKGROUND OF THE INVENTION

1. Scope of the Invention

This invention relates to the process of hydroformylating olefins with syngas in the presence of a novel catalyst composition to form aldehydes. More particularly, it relates to an improved olefin hydroformylation catalyst system comprising a mixture of (1) a platinum (0) complex containing two bidentate ligands; and (2) a Group IVB metal halide, each of which components is described in further detail below.

The novel organo metallic complex catalyst composition of this invention provides high reaction rates and high ratios of linear to branched aldehydes.

2. Description of the Prior Art

Processes of preparing aldehydes by hydroformylating an olefin with syngas, i.e., a mixture of hydrogen and carbon monoxide, in the presence of various catalysts, particularly cobalt and rhodium catalysts, is well known in the art. See, for example, Kirk-Othmer Encyclopedia of Chemical Technology ("OXO process"). Depending upon the catalyst, varying rates of reaction, and more importantly, different ratios of linear to branched aldehydes are obtained, the linear aldehydes being the preferred ones (as intermediates in the conversion, e.g., to alcohols by known hydrogenation methods and the like).

The use of platinum (II) complexes as hydroformylation catalysts in the OXO process, either alone, or in combination with $SnCl_2$, is known. Higher ratios of straight to branched aldehydes are obtained when tertiary phosphine-coordinated platinum complexes are used. For example, $PtH(SnCl_3)(PPh_3)_2$ is shown by Hsu and Orchin, *J. Amer. Chem Soc.*, 97, 353 (1975) to be useful for conversion of 1-pentene to aldehydes. Schwager and Knifton, *J. Cat.*, 45, 256 (1976), U.S. Pat. Nos. 3,981,925 and 3,996,293 disclose use of $PtCl_2(PPh_3)_2 + SnCl_2$ for a similar reaction with 1-heptene. Kawabata, et al., *J.C.S. Chem. Comm* 462 (1979) teach $Pt(PhCN)_2Cl_2 + Ph_2P(CH_2)_xPPh_2$ for conversion of 1-pentene to aldehydes. U.S. Pat. Nos. 4,101,565 and 4,155,939 show the dimer $(PtCl_2PPh_3)_2 + SnCl_2$ for hydroformylation of 1-hexene. U.S. Pat. No. 3,876,672 also shows hydroformylation of 1-hexene with $PtH(PPh_3)_3 + HSO_4^-$. See also, U.S. No. 4,405,496, which describes a platinum (acetylacetonate) in combination with a Group IVB metal halide and a tertiary phosphine. Other effective platinum (II) complexes include the ionic complexes shown in U.S. Pat. No. 3,876,672.

In addition, U.S. Pat. No. 4,370,258 teaches the combination of platinum (II) complexed with bidentate ligands, such as 1,2-bis(diphenylphosphinomethyl) cyclobutane ("DPMCB"), in combination with Group IVB metal halides, as hydroformylation catalysts.

Finally, earlier-filed application Ser. No. 491,687, filed May 5, 1983 in the name of Hsu, et al., and now Pat. No. 4,487,973 discloses the use of a mixture of a platinum (0) complex containing a monodentate ligand and a Group IVB metal halide as a hydroformylation catalyst.

The platinum (II) catalysts, although somewhat effective in favoring selective formation and high yields of the more desirable straight chain aldehydes, and sometimes at relatively mild conditions of temperature and pressure, nevertheless tend to reduce the reaction rate and therefore diminish the economic importance of the process. Moreover, the large proportion of halides in such catalysts introduces a considerable potential for corrosion of manufacturing equipment, thereby requiring large capital outlays for corrosion resistent equipment and lines, and thus reducing economic value of the catalysts.

SUMMARY OF THE INVENTION

In accordance with the present invention, there is provided a novel olefin hydroformylation organometallic catalyst system comprising:

(1) a platinum (0) complex containing two bidentate ligands, and having the general formula:

$$Pt(L)_2$$

wherein L is a bidentate ligand having one of the following formulas:

$$R_1R_2Q(CH_2)_mQR_3R_4;$$

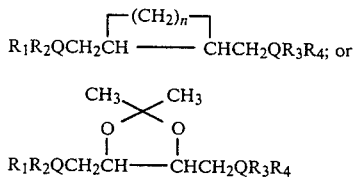

wherein Q is a Group VA metal, including arsenic, antimony, or preferably, phosphorus; $R_1, R_2, R_3,$ and $R_4$ are alkyl, aryl, alkoxyl, or aryloxyl, and may be the same or different; m is an integer of from 3 to about 5; and n is an integer of from 2 to about 4; and (2) A Group IVB metal halide of the type previously used in the art but which typically may have one of the following formulas:

$$MR_nX_{(4-n)}; MX_2; \text{ or } MX_4$$

wherein M is germanium, lead, or most preferably, tin; R is alkyl, alkoxyl, aryl, or aryloxyl, in which case n is an integer of from 1 to 3, or R is an anion derived from a diketone, a diacid, or a diester, in which case n is an integer of from 1 to 3 if the anion is a monoanion, or 1 n is 1 if the anion is a di-anion; and X is a halide, preferably chlorine. These halides may also include water of crystallization.

In the above formulas the R groups desirably contain one to six carbon atoms when alkyl, such as methyl, ethyl or hexyl; or six to twenty carbon atoms when aryl, such as phenyl, naphthyl, tolyl or the like. Alkyl and alkoxyl groups include cycloalkyl and cycloalkoxyl groups, while the aryl and aryloxyl groups include alkyl-substituted aromatic groups.

The invention is also directed the process of hydroformylating olefins with syngas in the presence of the aforedescribed catalysts to form aldehydes.

DESCRIPTION OF PREFERRED EMBODIMENTS OF THE CATALYST

The above-described catalyst of this invention is employed in a homogeneous system, the solvents for which may be selected from a wide range of solvents for the OXO reaction such as aromatic hydrocarbons, alkylaromatic hydrocarbons; alkyl, aryl, or alkylaryl ketones; or halogenated hydrocarbons. Illustrations of specific solvents include benzefne, toluene, xylenes, ethylbenzene, tetralin, acetone, methylethyl ketone, acetophenone, dichloroethane, and the like.

The catalyst complexation may be accomplished separately, but is most conveniently prepared in situ by simply mixing together in the desired solvent the two aforesaid catalyst components, and thereafter carrying out the olefin hydroformylation process in a generally known manner. When combining these components, the ratios of the components, based on their metal content, are desirably in the range of about 0.5:1 to 20:1, and preferably less than 5:1 molar ratio for the [Group IVB metal]/[Pt] ratio; and desirably in the range of from about 1:1 to 5:1, preferably less than 2:1 for the [P]/[Pt] molar ratio.

Although the reaction system is a homogeneous one, it has been found that the catalyst may readily be recovered and recycled with little or no loss of activity.

Examples of bidentate diphosphine ligands which may be complexed with platinum (0) to form the platinum (0) complex containing two such ligands include the following:

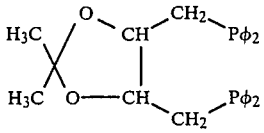

| $P\phi_2(CH_2)_3P\phi_2$ | Bis(1,3-diphenylphosphino-propane)(1,3-DPP) |
| $P\phi_2(CH_2)_4P\phi_2$ | Bis(1,4-diphenylphosphino-butane)(1,4-DPB) | wherein $\phi$ is a phenyl group.

The platinum (0) complexes containing the two bidentate ligands may conveniently be prepared by reducing a platinum salt such as $K_2PtCl_4$ with a base such as KOH in an alcohol-water solution in the presence of an excess of the desired bidentate diphosphine ligand and recovering the platinum (0) complex of the formula $Pt(L)_2$ as defined above. Specific illustrations of the preparation of such a complex are included in the examples below.

Examples of the Group IVB metal halides which may be employed in the preparation of the catalyst of the invention include:

diphenyl tin(IV)dichloride [$Sn(C_6H_5)_2Cl_2$],
tin(IV)dichlorodiacetylacetonate [$Sn(acac)_2Cl_2$],
tin(II)dichloride [$SnCl_2.2H_2O$ or $SnCl_2$],
tin(IV)tetrachloride [$SnCl_4$], and
phenyl tin(IV)trichloride [$Sn(C_6H_5)Cl_3$].

Illustrations of various combinations of the above two components used to form the novel catalyst complexes are also set forth below in the examples.

DESCRIPTION OF THE PROCESS

The hydroformylation of olefins with syngas in the presence of a catalyst is generally well-known (see the cited prior art-supra), and need not be repeated in detail herein.

Suffice it to say that the olefin starting material may be any olefin known in the art which can be hydroformylated. Examples of such olefins include $C_2$–$C_{20}$ aliphatic or cycloaliphatic monoolefins, and conjugated or non-conjugated aliphatic or cycloalaphatic diolefins which preferably are linear, but which may branched and/or substituted, including such substituted olefins as ethylenically unsaturated alcohols, aldehydes, ketones, esters and the like, as well as aromatic compounds whose ethylenically unsaturated side chain is capable of being hydroformylated such as styrene or allyl benzene. Where mixtures of olefins are employed, the process of this invention nevertheless generally results in the selective formation of linear aldehydes in major yields.

The reaction conditions are those generally employed in the art, and may vary widely depending upon the olefin and catalyst employed, but which typically include temperatures of from about 25°–125° C., preferably 75°–100° C.; pressures of from about 100–3000 psi, preferably 750–1500 psi; and a syngas ratio of $H_2/CO$ desirably in the range of from about 0.25 to 4 and more preferably 0.75 to 2.0 (molar ratio).

Finally, the concentration of catalyst complex employed in the reaction, based on the amount of metallic platinum in the complex, which may vary widely, is desirably in the range of from about $1\times10^{-5}$ to $1\times10^{-1}$ Mole, and more preferably $1\times10^{-3}$ to $2\times10^{-2}$ Mole, per mole of olefin present.

The hydroformylation process may be conducted in a batch, semi-continuous or continuous manner. Moreover, the process can be combined with hydrogenation of the aldehydes to alcohols by venting the reactor after aldehyde formation and introducing hydrogen under suitable conditions of temperature and pressure. The catalyst used for the hydroformylation can also be used for the hydrogenation or fresh catalyst can be added. Less preferably, the reactor is not vented and a large volume of hydrogen is introduced for admixture with syngas remaining from the hydroformylation.

The invention will now be illustrated by, but is not intended to be limited to, the following examples.

EXAMPLE 1

This example describes the hydroformylation of propylene to butyraldehyde in the presence of catalysts of the present invention: An autoclave was charged under nitrogen atmosphere with 100 ml of p-xylene, 0.596 g (0.5 mmole) of Pt[(−)-DIOP]$_2$ and 0.76 g of $\phi SnCl_3$, where $\phi$ is phenyl, and DIOP is 2,3-o-isopropylidene - 2,3-dihydroxy- 1,4-bis(diphenylphosphino)butane. The autoclave was first purged with syngas ($H_2/CO=1/1$) then pressured to about 400 psig with syngas and stirred for 0.5 hr. The contents of the autoclave were then quickly heated to 100° C. and 10.5 g. (249 mmole) of propylene was added, whereupon the pressure was adjusted to 1000 psig. After about 10 min. decreasing pressure indicated that the reaction had begun. (This 10 min. period is the induction time). The pressure was maintained at 1000 psig by means of a syngas reservoir. After 1 hr. the autoclave was quickly cooled and the liquid mixture analyzed using vapor phase chromatography. Analysis of the data indicated a yield of $C_4$-aldehydes equal to 85% and the ratio of n-butyraldehyde to iso-butyraldehyde to be 4 to 1, corresponding to 80% of linear butyraldehyde. The results are summarized in Table I below.

EXAMPLES 2-5

In these examples, also shown in Table I, the reaction procedures were similar to those used in Example I, except that different tin halides and different bidentate diphosphine ligands were used.

TABLE I

|  | EXAMPLE 1 | EXAMPLE 2 | EXAMPLE 3 | EXAMPLE 4 | EXAMPLE 5 |
|---|---|---|---|---|---|
| REAGENTS | | | | | |
| Propylene | 249 mmole | 256 mmole | 250 mmole | 258 mmole | 251 mmole |
| Pt Complex | 0.5 mmole | 0.5 mmole | 0.5 mmole | 0.2 mmole | 0.5 mmole |
|  | Pt(DIOP)$_2$ | Pt(DIOP)$_2$ | Pt(DIOP)$_2$ | Pt(DPMCB)$_2$[(2)] | Pt[$\phi_2$P(CH$_2$)$_3$P$\phi_2$]$_2$ |
| Sn Compound | 2.5 mmole | 2.5 mmole | 2.5 mmole | 1.0 mmole | 2.5 mmole |
|  | $\phi$SnCl$_3$ | SnCl$_2$.2H$_2$O | SnCl$_4$ | $\phi$SnCl$_3$ | $\phi$SnCl$_3$ |
| P-xylene | 100 ml | 100 ml | 100 ml | 100 ml | 100 ml |
| H$_2$/CO (1:1) | 1000 psig | 1000 psig | 1000 psig | 1000 psig | 1000 psig |
| CONDITIONS | | | | | |
| Temperature | 100° C. | 100° C. | 100° C. | 100° C. | 100° C. |
| Reaction Time[(1)] | 1 hr. | 3 hr. | 1 hr. | 1 hr. | 2 hr. |
| RESULTS | | | | | |
| Yield of C$_4$—Aldehydes | 85% | 82% | 90% | 92% | 51% |
| Ratio of n/iso-Butyraldehyde | 80/20 | 82/18 | 81/19 | 90/10 | 66/34 |

[(1)]Induction Period (varied from 5-25 min.) is not included.
[(2)]DPMCB = trans-bis(1,2-diphenylphosphinomethyl)cyclobutane.

EXAMPLE 6

The following example illustrates the preparation of Pt[(−)DIOP]. Each of the other platinum (0) complexes of this invention containing two bidentate diphosphine ligands may be prepared in a like manner.

To a 1.0 liter three-necked round bottom flask fitted with a standard additional funnel and thermometer and under nitrogen atmosphere was added 500 ml of degassed ethanol and 8.97 g. of (−) DIOP. The contents were heated to 65° with stirring and then 5.0 g. of KOH in 100 ml of 1/1 ethanol/water was added. After the reaction solution became clear, a degassed solution of 2.7 g. K$_2$PtCl$_4$ in 100 ml of water was added through the addition funnel at a moderate rate. After the addition, the reaction solution turned yellow, and the solution was cooled with an ice-water bath. The yellow precipitates were then filtered and washed successively with water, hot ethanol, and cold ethanol, and then dried in vacuo. The yield was 7.20 g. of Pt[(−) DIOP]$_2$ m.p. 190°-192° C. (Dec.). Positive structure identification was made by using $^{13}$C and $^{31}$P-NMR methods of analysis.

EXAMPLE 7

In accordance with the procedures of Example 1, except that 1-butene is substituted propylene, and Sn(C$_6$H$_5$)$_2$Cl$_2$ for Sn(C$_6$H$_5$)Cl$_3$, there is obtained linear 1-pentanal in good yield and selectively over the corresponding branched aldehyde.

In a like manner, but substituting 1-pentene for propylene, and Pt(2,3-o-isopropylidene-2,3-dihydroxy-1,4-bis(di-p-tolylphosphino) butane)$_2$ for Pt(DIOP)$_2$, the corresponding linear 1-hexanal is obtained in good yield and selectively.

EXAMPLE 8

In accordance with the procedures of Example 2, but substituting 2-pentene for propylene, and Pt(2,3-o-isopropylidene-2,3-dihydroxy-1,4-bis(di-o-tolylphosphino)butane))$_2$ for Pt(DIOP)$_2$, there is obtained linear 1-hexanal in good yield and selectively over the corresponding branched aldehyde.

In a like manner, but substituting styrene for propylene, the corresponding linear 3-phenylpropanal is obtained in good yield and selectively.

EXAMPLE 9

In accordance with the procecures of Example 4, but substituting α-methylstyrene for propylene, and Pt(cis-1,2-bis(di-p-tolylphosphenomethyl)cyclobutane)$_2$ for Pt(DPMCB)$_2$, there is obtained linear 3-phenylbutryaldehyde in good yield and selectively over the corresponding branched aldehyde.

In a like manner, but substituting allylbenzene for propylene, and Pt(trans-1,2-bis(di-o-tolylphosphinomethyl)cyclobutane)$_2$ for Pt(DPMCB)$_2$, the corresponding linear 4-phenylbulyraldehyde is obtained in good yields and selectively.

What we claim is:

1. A catalyst system for hydroformylation of olefins, which comprises (1) a platinum (0) complex containing two bidentate diphosphine, diarsine or distibine ligands, and (2) a Group IVB metal halide.

2. The composition of claim 1 wherein the platinum (0) complex has the general formula:

Pt(L)$_2$ wherein L is a bidentate ligand having one of the following formulas:

R$_1$R$_2$Q(CH$_2$)$_m$QR$_3$R$_4$;

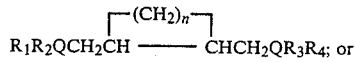
R$_1$R$_2$QCH$_2$CH ——— CHCH$_2$QR$_3$R$_4$; or

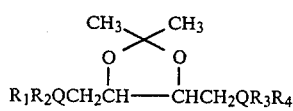
R$_1$R$_2$QCH$_2$CH——CHCH$_2$QR$_3$R$_4$ wherein Q is arsenic, antimony, or phosphorus; R$_1$, R$_2$, Rhd 3, and R$_4$ are alkyl, aryl, alkoxyl, or aryloxyl and may be the same or different; m is an integer of from 3 to about 5; and n is an integer of from 2 to about 4.

3. The composition of claim 1 wherein the Group IVB metal halide has one of the following formulas:

MR$_n$X$_{(4-n)}$; MX$_2$; or MX$_4$ wherein M is germanium, lead or tin; R is alkyl, alkoxyl, aryl, or aryloxyl in which case n is an integer of from 1 to 3, or R is an anion derived from a diketone, a diacid, or a diester, in which case n is an integer of from 1 to 3 if the anion is a mono-anion, or n is 1 if the anion is a di-anion; and X is a halide.

4. The composition of claim 1 wherein the molar ratio of the Group IVB metal to platinum is in the range of about 0.5:1 to 20:1 and the ratio of phosphorus to platinum is in the range of from about 1:1 to 30:1.

5. The composition of claim 1 wherein the platinum (0) complex is platinum (2,3-o-isopropylidene-2,3-dihydroxy-1,4-bis(diphenylphosphino)butane)$_2$; and the Group IVB metal halide is SnCl$_2$.

6. The composition of claim 1 wherein the platinum (0) complex is platinum(trans-bis(1,2-diphenylphosphinomethyl)cyclobutane)$_2$; and the Group IVB metal halide is SnCl$_2$.

7. The composition of claim 1 wherein the platinum (0) complex is platinum(2,3-o-isopropylidene-2,3-dihydroxy-1,4-bis(diphenylphosphino) butane)$_2$; and the Group IVB metal halide is Sn(C$_6$H$_5$)$_2$Cl$_2$.

8. The composition of claim 1 wherein the platinum (0) complex is platinum(trans-bis(1,2-diphenylphosphinomethyl)cyclobutane)$_2$; and the Group IVB metal halide is Sn(C$_6$H$_5$)$_2$Cl$_2$.

9. The composition of claim 1 wherein the platinum (0) complex is platinum(2,3-o-ispropylidene-2,3-dihydroxy-1,4-bis(diphenylphosphino) butane)$_2$; and the Group IVB metal halide is Sn(acetylacetonate)$_2$Cl$_2$.

10. The composition of claim 1 wherein the platinum (0) complex is platinum(trans-bis(1,2-diphenylphosphinomethyl)cyclobutane)$_2$; and the Group IVB metal halide is Sn(acetylacetonate)$_2$Cl$_2$.

11. The composition of claim 1 wherein the platinum (0) complex is platinum(2,3-o-isopropylidene-2,3-dihydroxy-1,4-bis(diphenylphosphino) butane)$_2$; and the Group IVB metal halide is Sn(C$_6$H$_5$)Cl$_3$.

12. The composition of claim 1 wherein the platinum (0) complex is platinum(trans-bis(1,2-diphenylphosphinomethyl)cyclobutane)$_2$; and the Group IVB metal halide is Sn(C$_6$H$_5$)Cl$_3$.

* * * * *